US00PP15908P2

(12) United States Plant Patent
Jonkers

(10) Patent No.: US PP15,908 P2
(45) Date of Patent: Aug. 2, 2005

(54) **DOUBLE *IMPATIENS* PLANT NAMED 'DIDI SALMON TWO'**

(50) Latin Name: *Impatiens walleriana*
Varietal Denomination: Didi Salmon Two

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 110 days.

(21) Appl. No.: 10/818,357

(22) Filed: Apr. 5, 2004

(51) Int. Cl.[7] ..... A01H 5/00
(52) U.S. Cl. ..... Plt./317
(58) Field of Search ..... Plt./317

(56) References Cited

PUBLICATIONS

UPOV–ROM GTITM Plant Variety Database, 2004/04 GTI Jouve Retrieval Software, Citation for Impatiens 'Didi Salmon Two'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of Double *Impatiens* plant named 'Didi Salmon Two', characterized by its compact, upright, outwardly spreading and mounded plant habit; freely branching growth habit; dark green-colored leaves; freely flowering habit; and light red-colored flowers that are fully double and positioned above and beyond the foliage.

1 Drawing Sheet

Botanical classification/cultivar designation: *Impatiens walleriana* cultivar Didi Salmon Two.

BACKGROUND OF THE INVENTION

The present Invention relates to a new and distinct cultivar of Double *Impatiens* plant, botanically known as *Impatiens walleriana*, and hereinafter referred to by the name 'Didi Salmon Two'.

The new Double *Impatiens* is a product of a planned breeding program conducted by the Inventor in Andijk, The Netherlands. The objective of the breeding program was to develop new compact Double *Impatiens* cultivars with fully double flowers, freely branching and flowering habit, early flowering and attractive flower and foliage coloration.

The new *Impatiens* originated from a cross-pollination made by the Inventor in March, 2000, of a proprietary *Impatiens walleriana* selection identified as code number IW-522-1, not patented, as the female, or seed parent, with a proprietary *Impatiens walleriana* selection identified as code number IDT-32-49, not patented, as the male, or pollen parent. The cultivar Didi Salmon Two was discovered and selected by the Inventor as a flowering plant within the progeny of the stated cross-pollination in a controlled environment in Andijk, The Netherlands in September, 2000.

Asexual reproduction of the new cultivar by terminal cuttings in Andijk, The Netherlands since September, 2000, has shown that the unique features of this new *Impatiens* are stable and reproduced true to type in successive generations of asexual reproduction.

SUMMARY OF THE INVENTION

The following traits have been repeatedly observed and are determined to be the unique characteristics of 'Didi Salmon Two'. These characteristics in combination distinguish 'Didi Salmon Two' as a new and distinct Double *Impatiens* cultivar:

1. Compact, upright, outwardly spreading and mounded plant habit.
2. Freely branching growth habit.
3. Dark green-colored leaves.
4. Freely flowering habit.
5. Light red-colored flowers that are fully double and positioned above and beyond the foliage.

Plants of the new *Impatiens* differ primarily from plants of the female parent selection in the following characteristics:

1. Plants of the new *Impatiens* are more compact than and not as compact as plants of the female parent selection.
2. Plants of the new *Impatiens* have larger flowers than plants of the female parent selection.
3. Plants of the new *Impatiens* have fully double flowers whereas plants of the female parent selection have semi-double flowers.
4. Plants of the new *Impatiens* and the female parent selection differ in flower color as plants of the female parent selection have white-colored flowers.

Plants of the new *Impatiens* differ primarily from plants of the male parent selection in the following characteristics:

1. Plants of the new *Impatiens* have fully double flowers whereas plants of the male parent selection have single flowers.
2. Plants of the new *Impatiens* and the male parent selection differ in flower color as plants of the male parent selection have white-colored flowers.

Plants of the new *Impatiens* differ primarily from plants of the cultivar Didi Carmine Two, disclosed in a U.S. Plant patent application Ser. No. 10/818,343 filed concurrently, in flower color.

The new *Impatiens* can be compared to the *Impatiens walleriana* cultivar Balolesal, disclosed in U.S. Plant Pat. No. 13,648. However, in side-by-side comparisons conducted in Gilroy, Calif., plants of the new *Impatiens* differed from plants of the cultivar Balolesal in the following characteristics:

1. Leaves of plants of the new *Impatiens* were broader and shorter than leaves of plants of the cultivar Balolesal.
2. Flowers buds of plants of the new *Impatiens* were more coral in color than flowers buds of plants of the cultivar Balolesal.
3. Sepals of plants of the new *Impatiens* were larger than sepals of plants of the cultivar Balolesal.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Impatiens*.

The photograph at the top of the sheet comprises a side perspective view of a flowering plant of 'Didi Salmon Two'.

The photograph at the bottom of the sheet is close-up view of typical flowers and leaves of 'Didi Salmon Two'.

DETAILED BOTANICAL DESCRIPTION

Plants of the cultivar Didi Salmon Two have not been observed under all possible environmental conditions. The phenotype may vary somewhat with variations in environment such as temperature and light intensity, without, however, any variance in genotype. The aforementioned photographs and following observations and measurements describe plants grown in Gilroy, Calif., under commercial practice in a fiberglass-covered greenhouse during the late spring with day temperatures about 27 to 29° C., night temperatures about 16 to 18° C. and light levels about 2,000 foot-candles. Rooted young plants were planted in containers and had been growing for about five months when the photographs and the description were taken. In the following description, color references are made to The Royal Horticultural Society Colour Chart, 1995 Edition, except where general terms of ordinary dictionary significance are used.

Botanical classification: *Impatiens walleriana* cultivar Didi Salmon Two.

Parentage:

*Female parent.*—Proprietary *Impatiens walleriana* selection identified as code number IW-522-1, not patented.

*Male parent.*—Proprietary *Impatiens walleriana* selection identified as code number IDT-32-49, not patented.

Propagation:

*Type cutting.*—Terminal cuttings.

*Time to initiate roots.*—About 10 to 21 days at 22 to 23° C.

*Time to produce a rooted young plant.*—About 28 days at 16 to 24° C.

*Root description.*—Fine, fleshy; white in color.

*Rooting habit.*—Freely branching.

Plant description:

*General appearance.*—Compact, upright, outwardly spreading and mounded plant habit.

*Growth and branching habit.*—Vigorous and freely-branching growth habit with about eight basal branches; lateral branches potentially forming at every node; dense and bushy growth. Pinching enhances branching.

*Plant height.*—About 20 cm.

*Plant diameter or spread.*—About 45 cm.

*Lateral branches.*—Length: About 24 cm. Diameter: About 1.2 cm. Internode length: About 3 cm. Texture: Smooth, glabrous. Color: 146B with splotches of 185B.

*Foliage description.*—Arrangement: Alternate, simple. Length: About 6.3 cm. Width: About 4.3 cm. Shape: Elliptical. Apex: Acuminate. Base: Attenuate. Margin: Crenate with sparse ciliation. Texture, upper and lower surfaces: Smooth, glabrous. Venation pattern: Pinnate. Color: Developing and fully expanded foliage, upper surface: Darker than 147A. Developing and fully expanded foliage, lower surface: 147B. Venation, upper surface: 147A to 147B. Venation, lower surface: 147B. Petiole: Length: About 1.8 cm. Diameter: About 3 mm. Texture, upper and lower surfaces: Smooth, glabrous. Color: 147B.

Flower description:

*Flower type and habit.*—Numerous and consistently double flowers. Flower buds open similar to a rose in fullness; flowers rounded in shape. Flowers arise from leaf axils. Freely flowering, usually about 25 flowers and flower buds per lateral branch. Flowers positioned above the foliage and typically face upright or outward. Flowers last about five to seven days under greenhouse conditions. Flowers not persistent. Flowers not fragrant.

*Natural flowering season.*—Flowering is continuous through the spring and summer.

*Flower size.*—Diameter: About 4.2 cm. Depth: About 1.7 cm.

*Flower buds* (*at stage of showing color*).—Length: About 1.6 cm. Diameter: About 1.2 cm. Shape: Ovoid. Color: 52D.

*Petals.*—Quantity/arrangement: About 24 per flower; imbricate. Length, outermost petals: About 2.3 cm. Width, outermost petals: About 1.8 cm. Length, innnermost petals: About 7 mm. Width, innermost petals: About 6 mm. Shape: Obovate to cordate. Apex: Rounded and occasionally emarginate. Base: Acute. Margin: Entire. Texture, upper and lower surfaces: Smooth, glabrous. Color: When opening, upper surface: Brighter than 50A. When opening, lower surface: 50B to 50C. Fully opened, upper surface: More rose than 43C. Fully opened, lower surface: 50C.

*Sepals.*—Quantity/arrangement: Five in a single whorl; one modified into an elongated spur. Calyx length: About 1 cm. Calyx diameter: About 1 cm. Shape: Elliptic. Apex: Acute. Margin: Entire. Texture, upper and lower surfaces: Smooth, glabrous. Color, upper and lower surfaces: Close to 144A. Spur length: About 3 cm. Spur diameter: At flower, about 2 mm; at apex, less than 1 mm. Spur color: 144A to 144B.

*Peduncles.*—Length: About 2.7 cm. Diameter: About 2 mm. Angle: About 45° from vertical. Strength: Strong. Texture: Smooth, glabrous. Color: 144A.

*Reproductive organs.*—None observed.

*Seed/fruit.*—None observed.

Disease/pest resistance: Plants of the new *Impatiens* have not been observed to be resistant to pathogens and pests common to *Impatiens*.

It is claimed:

1. A new and distinct cultivar of Double *Impatiens* plant named 'Didi Salmon Two', as illustrated and described.

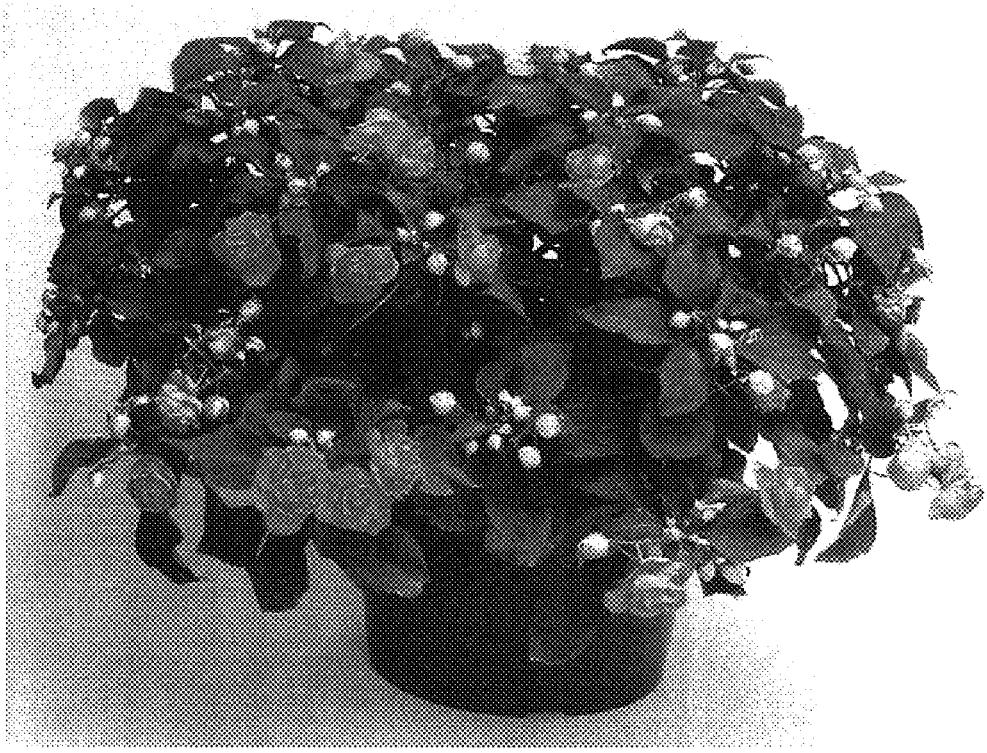
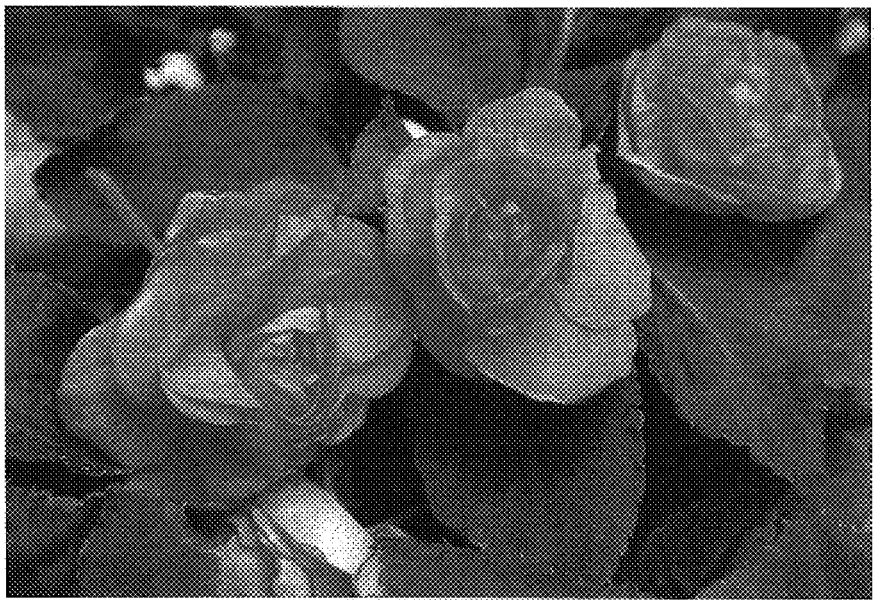

* * * * *